United States Patent [19]

Minks

[11] 4,203,574
[45] May 20, 1980

[54] FLUID FLOW MEASUREMENT APPARATUS

[76] Inventor: Floyd M. Minks, 2700 Partin Settlement Rd., Kissimmee, Fla. 32741

[21] Appl. No.: 834,716

[22] Filed: Sep. 19, 1977

Related U.S. Application Data

[63] Continuation-in-part of Ser. No. 635,221, Nov. 25, 1975, Pat. No. 4,054,054.

[51] Int. Cl.² ............................................. F16K 31/06
[52] U.S. Cl. .................................... 251/139; 251/141; 251/144
[58] Field of Search ..................... 251/139, 141, 144

[56] References Cited

U.S. PATENT DOCUMENTS

| | | | |
|---|---|---|---|
| 2,561,922 | 7/1951 | Hall | 251/139 |
| 2,616,452 | 11/1952 | Clay et al. | 251/139 |
| 2,637,344 | 5/1953 | Matthews | 251/139 |
| 3,833,015 | 9/1974 | Kneuer | 251/139 X |
| 3,861,644 | 1/1975 | Knape | 251/129 X |

Primary Examiner—Arnold Rosenthal
Attorney, Agent, or Firm—Duckworth, Hobby & Allen

[57] ABSTRACT

A device for indicating the interval for the flow of a predetermined volume of fluid. The fluid flow measurement device includes a housing having a cavity therein for being interposed along a fluid line. A flexible diaphragm having a convolution therein is included within the cavity for dividing the cavity into a first and second chamber. The flexible diaphragm prevents the flow of the fluid between the first and second chambers. A fluid port connects the second chamber to the fluid flow line. A fluid outlet connects the first chamber to the fluid flow line. The apparatus also includes a bypass for diverting the fluid flow from the fluid port of the second chamber through a fluid inlet into the second chamber, whereby the fluid flowing into the second chamber will displace the flexible diaphragm into the first chamber thereby expelling the predetermined volume of fluid from the first chamber.

4 Claims, 6 Drawing Figures

FLUID FLOW MEASUREMENT APPARATUS

This application is a continuation-in-part of application Ser. No. 635,221, filed on Nov. 25, 1975, and now U.S. Pat. No. 4,054,054.

BACKGROUND OF THE INVENTION

1. Field of the Invention

This invention relates to a fluid flow meter for indicating the rate of flow through a fluid transport line and in particular the rate of flow of a liquid fuel being consumed by an internal combustion engine.

2. Description of the Prior Art

One common method of measuring the fuel consumption of an internal combustion engine is to cause the fuel to flow through a vertically oriented tapered tube having a movable member therein. As the fuel flow rate increases the differential pressure forces the movable member into a higher position within the tube where a correspondingly larger space is available for fuel to flow around the movable member. While this method is quite satisfactory for research and development projects on internal combustion engines, it is rather impractical for consumer operated motor vehicles. Various electronic methods of sensing the position of the movable member of this type have been proposed but are generally either too expensive, too inaccurate, or both.

Another well known method of measuring fuel flow rate is to pass the fuel over the blades of a turbine or through a vane-type metering device similar to a vane pump. In actual construction, these devices have a relatively limited range of flow rates for which useful accuracy can be expected. Inaccuracies generally arise due to the wide pressure variations present under ordinary operating conditions or the bearing friction inherent in most turbine designs. Furthermore, the analog read-out devices most easily adapted and normally used with fuel flow metering devices of this type are either inherently expensive, relatively inaccurate or both. These devices are typically difficult to use due to the short term fuel flow variations inherent in the stop-and-go urban traffic patterns. It is difficult if not completely impossible to translate these short term variations into a long term fuel flow average value.

Another method commonly used for test track evaluation of fuel flow is to install a three way valve between the fuel pump inlet and the gas tank with a third port connected to a graduated cylinder of known volume, such as one-tenth of a gallon. The driver manually operates these valves and visually observes the rate of fuel consumption from the graduated container. The valve must then be returned to the fuel tank position and the graduated cylinder refilled or the engine will stop running due to a lack of fuel. The convenience of this fuel flow measuring device leaves much to be desired since the graduated container must be filled by manual techniques. Even though this type of fuel flow measuring device is extremely accurate over a very wide range of flow rates, it is obviously impractical and in some cases unsafe for use on a vehicle operating under normal highway conditions.

It is therefore the object of this invention to produce a simple and inexpensive device, capable of accurately indicating the fuel consumption of an engine over a very wide range of engine sizes and operating conditions without the requirement of extensive fuel system modifications. It is a further object of this invention that no manual operations be required of the operator at any time subsequent to the initiation of the metering interval, which, if neglected, could cause the engine to stop running for a lack of fuel.

It is a further object of this invention to eliminate analog read-out devices since they are relatively expensive, inaccurate and difficult to interpret under normal operating conditions. Another object of this invention is that the fuel flow measurement apparatus must operate with a pressure drop which is small enough under all conditions so as to be negligible when compared to the pressure available from normal automotive fuel pumps.

SUMMARY OF THE INVENTION

This invention relates to an improved device for indicating the interval for the flow of a predetermined volume of fluid. The apparatus includes a chamber for being interposed in a fluid flow line, a movable member within the chamber, and means for connecting the chamber on one side of the movable member to a fluid outlet, with the chamber on one side of the movable member containing at least a predetermined volume of fluid. The apparatus also includes means for connecting the chamber on another side of the movable side to a fluid port for coupling to the fluid flow line, means for effecting fluid flow through the fluid port into the chamber adjacent the other side of the movable member for moving the member to expel the predetermined volume of fluid through the fluid outlet, and indicating means for indicating the interval required for removing the predetermined volume of fluid from the chamber adjacent to one side of the movable member. The improvement to this apparatus comprises a flexible diaphragm having a convolution therein. The flexible diaphragm is coupled between the chamber and the movable member for preventing the flow of fluid within the chamber between one side of the movable member and the other side of the movable member.

DETAILED DESCRIPTION OF THE PREFERRED EMBODIMENT

I. Fuel Flow Measurement Apparatus

Figure 1:
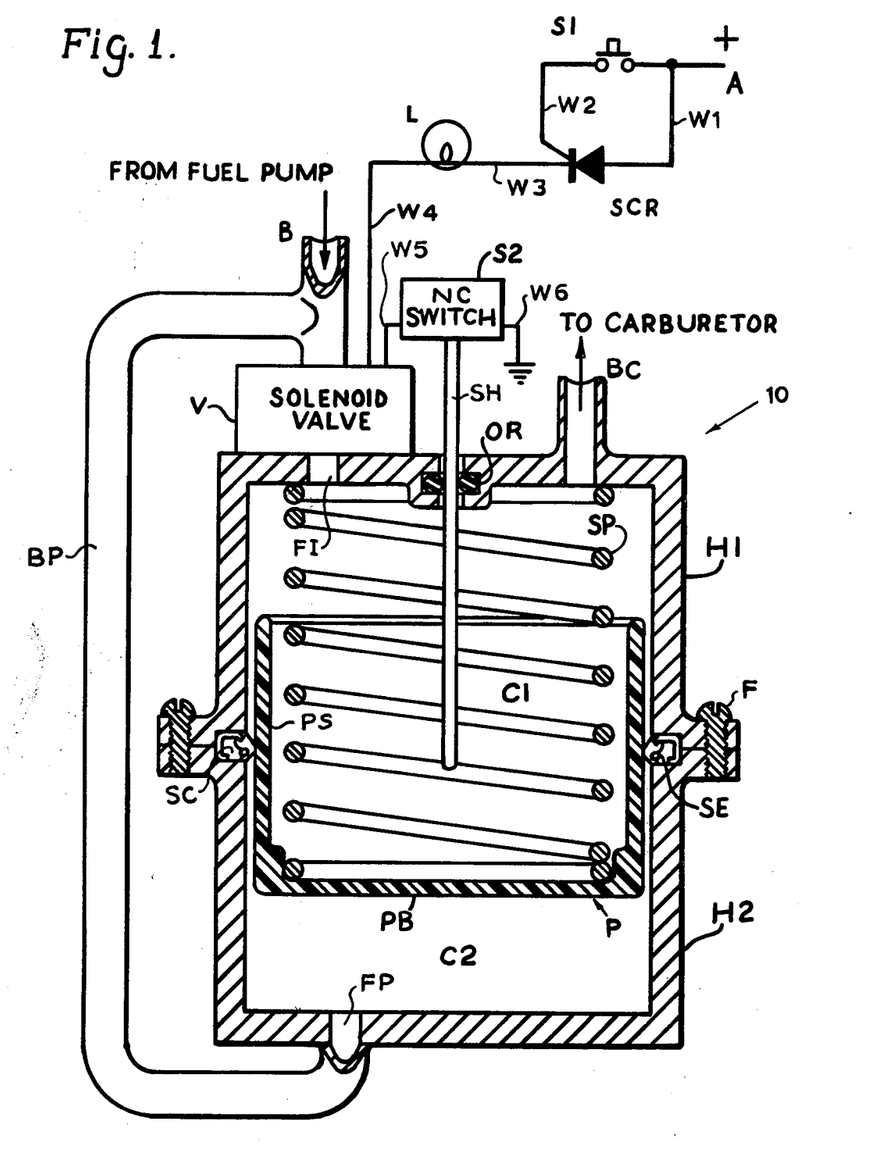
FIG. 1 shows a frontal cross section view of a first preferred embodiment of the fluid flow measurement apparatus.

An apparatus for indicating the interval for the flow of a predetermined volume of a fluid through a fluid flow line is referred to generally as 10 in FIG. 1. A fluid or fuel flow line B which transports fuel from the fuel pump (not shown) couples with an electrically operated, normally open solenoid valve V. The valve V (or interrupting means or averting means) is coupled to the planar end of a generally cylindrical first housing H1 at a first fuel inlet FI. The first housinng H1 is congruently coupled at an abutting circumferential surface with a second generally cylindrical housing H2. The housings H1 and H2 define therein a generally cylindrical internal cavity having a generally cylindrical piston P (or movable member) congruently coupled for longitudinal movement therein. The piston P has a generally planar base PB with perpendicularly upstanding sides PS circumferentially therearound. The sides PS of the piston P slidingly communicate along a seal SE which is coupled in a recessed circumferential slot between the coupling of the first and second housings H1 and H2 respectively. The piston base PB further divides the internal cavity defined by the housings H1 and H2 into a first cavity C1 on one side of the piston P and a second cavity C2 on the other side of piston P. Cavity C1 includes the predetermined volume of fuel and further includes the volume defined by the piston base PB and the upstanding piston sides PS. Another fuel flow line or outlet line BC is coupled to the upper planar surface of the first housing H1 and communicates from the first cavity C1 to a carburetor (not shown). A fuel bypass line BP is coupled to the fuel line B adjacent to the solenoid valve V. The fuel bypass line also is coupled to the second cavity C2 through a fuel port FP in the lower planer surface of the second housing H2.

A shaft SH communicates through the planar surface of the first housing H1 at an O-ring OR and into the first cavity C1. The shaft SH is coupled to a normally closed switch S2 (or reset means). The length of the shaft SH is determined such that as piston P moves upwardly through cavity C1, the shaft SH will communicate with the bottom surface PB of the piston P as the sides PS of the piston approach the upper planar surface of the housing H1. A compression spring SP located within the first cavity C1 communicates with the upper planar surface of the housing H1 and the base PB of the piston P, thereby biasing the piston P to its furtherest longitudinal extension within the second cavity C2. At this furthermost longitudinal extension, the volume of the first cavity C1 is approximately one-tenth of a U.S. gallon plus the volume contained within the generally cylindrical piston sides PS. Stating this another way, when piston P is fully extended into the second cavity C2, the volume defined by the internal cavity within the first housing H1 from the upper planar surface thereof to the upper circumferential surface of the piston sides Ps is equal to one-tenth of a U.S. gallon. Of course, other predetermined volumes may be used, such as 0.1 liter, etc.

A circuit line W1 connects the anode of a silicon controlled rectifier SCR (or latching means) to a source of direct current energy A, such as the battery of an automobile. Of course a relay could be substituted for the SCR. A normally open switch S1 (or activating means) is coupled betweenn the supply of direct current energy A and a control element (or gate) of the silicon controlled rectifier SCR by a circuit element W2. A cathode of the SCR is coupled to the first lead of a light emitting element L (or indicating means), such as a tungsten filament lamp or a light emitting diode, by a wire W3. The second lead of the light L is coupled by a wire W4 to the first terminal of the coil of the solenoid operated valve V. The second terminal of the coil of the solenoid operated valve V is coupled by a wire W5 to one of the terminals of the normally closed switch S2. The other terminal of the normally closed switch S2 is coupled to ground by a wire W6. The switch S1, the silicon controlled rectifier SCR and the light L are normally located on the dash in the passenger compartment of the automobile, with only wire W4 communicating through the firewall to the valve V.

The operation of the fuel flow measurement apparatus 10 will now be described with continuing reference to FIG. 1. The fuel pump (not shown) pumps the fluid fuel, such as gasoline, through the fuel line B and into the first cavity C1. The spring SP forces the piston P into the second cavity C2 and longitudinally toward the fuel port FP. This motion of the piston P forces any residual fuel within the second cavity C2 to be expelled through the fuel port FP for transfer through the bypass line BP into the first cavity C1. The piston P is guided in its longitudinal movement through the generally cylindrical first and second cavities C1 and C2 by the coupling between the sliding seal SE and the upstanding piston sides PS. The slidable coupling prevents the flow of fuel between the first and second cavities C1 and C2 while allowing the piston to move therebetween. When the piston P reaches the limit of its longitudinal motion the piston base PB will be adjacent to the fuel port FP. This corresponds to a ready condition of the fuel flow measurement apparatus.

Assume the following: cavity C1 contains at least the predetermined volume of fuel, the silicon controlled rectifier SCR is in the off or non-conductive condition, and that valve V is de-energized (open). Therefore, spring SP is forcing piston P into the full down position resting against housing H2. The apparatus will remain in this state with fuel flowing from the inlet B, through the valve V and into the chamber H1 and then through outlet BC and thus to the carburetor of the internal combustion engine. A momentary closure of the switch S1 will cause a positive voltage to be placed on the gate of the SCR, which will enable the flow of current from the anode through the cathode of the SCR. This current will cause the lamp L to be lighted and will actuate the solenoid valve V to close or block the first fuel inlet FI. The closure of the solenoid valve V will cause the fuel to flow through the bypass line BP and into the second cavity C2 through the fuel port FP. The pressure provided by the fuel pump will be exerted upon the base PB of the piston P. As the carburetor continues to consume the fuel, additional fuel will be available through the fuel line BC from the first cavity C1. This displacement of fuel from the first cavity C1 is caused by the pressure on the base PB of the piston which causes a longitudinal movement motion of the piston P from the cavity C2 and into the cavity C1, thus overcoming the biasing pressure of the spring SP. Since the area of the piston P may be typically ten square inches and the force of the spring SP is typically two pounds, a restraining pressure of typically 0.2 pounds per square inch is encountered by the fuel flowing to the carburetor. This is negligible compared to the pressure produced by typical engine fuel pumps.

As the carburetor continues to consume the fuel the piston P will continue its motion into the first cavity C1 with the second cavity C2 filling with fuel flowing through the bypass line BP. As the sides PS of the piston P approach the upper planar surface of the first housing H1 the shaft SH will approach the piston base PB. When the piston base PB communicates with the shaft SH the normally closed switch S2 will be opened momentarily thus breaking the electrical circuit between the supply of direct current energy A and electrical ground. This momentary current interruption will turn off the SCR, cause the light L to be extinguished and cause the valve V to return to the open condition. Since S1 was only momentarily closed to actuate this process, the SCR will be non-conductive until S1 is again closed. As the solenoid operated valve V opens the fuel will again flow through the first fuel inlet FI from the fuel pump. The biasing force exerted upon the piston base PB by the spring SP will cause the piston P to move from the first cavity C1 and toward the second cavity C2, thus expelling the fuel within the second cavity C2 into the first cavity C1 through the bypass line BP. It should be understood that switch S2 or other limit sensing means might be located within the cavity and the required wires routed through housing H1. The switch would then be required to operate in the fluid medium.

Therefore, the period during which the light L is lighted corresponds to the period required for a known and predetermined volume of fuel to be expelled from the first cavity C1 into the carburetor through the fuel line BC. If this known volume of fuel is one-tenth of a gallon, it will be possible to measure the fuel economy of the internal combustion engine by utilizing the following method. As the odometer of the automobile approaches a convenient figure (such as 0.0) the first switch S1 is depressed thereby closing the solenoid valve V and lighting the light L. After the internal combustion engine consumes the one-tenth gallon of fuel from the first cavity C1, the piston base PB will communicate with the shaft SH thereby opening the normally closed switch S2 and extinguishing the light L. This will be the signal for the driver to again refer to the odometer to obtain the distance traveled during that period of time. For example, if the odometer reads 3.4 miles, then the automobile will have traveled 3.4 miles on 0.1 gallons of fuel, thus indicating a fuel consumption of 34 miles per gallon. Using this method the driver of the automobile may easily calculate the fuel economy of the internal combustion engine during periods of highway travel, suburban driving, or city driving by merely observing the number of miles traveled on the predetermned volume of fuel.

It should be noted at this point that after the predetermined volume of fuel within the first cavity C1 has been consumed by the engine, additional fuel will immediately flow through the first fuel inlet FI into the cavity C1 and out of the fuel flow line BC to the carburetor. Thus, there will be no gaseous spaces introduced into the fuel line BC since the first cavity C1 is not completely emptied of its fuel content. Therefore, there is no reason for the internal combustion engine propelling the car to miss, cough or sputter due to the lack of fuel.

Figure 2:
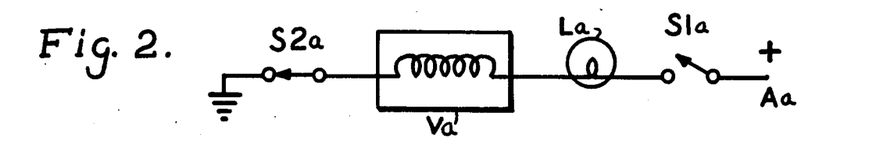
FIG. 2 shows an alternate electrical schemmatic diagram for the fluid flow indicating apparatus.

FIG. 2 pictorially represents a second electrical circuit which may be used to indicate the interval required for the flow of the predetermined volume of fuel out of the first cavity C1 and into the carburetor through the fuel flow line BC. A switch S1a is coupled to a light La which in turn is coupled to a solenoid valve Va. The solenoid valve Va is in turn coupled to a normally closed switch S2a and then to electrical ground. It will be noted that the switch S1a is a single pole, single throw switch rather than the momentary switch used in FIG. 1. The functions of light La, the solenoid operated valve Va and switch S2a remains unchanged. The fuel flow measurement apparatus is operated by closing the switch S1a. At the end of the metering interval, S2a will be actuated by the piston base PB contacting the shaft SH and thus opening the normally closed switch S2a.

The opening of the switch S2a will interrupt the flow of direct current through the lamp La thus opening the solenoid valve Va. Piston P will then start to move toward the second cavity C2 and the fuel port FP. This movement will cause the piston base PB to lose contact with the shaft SH, thereby again closing the normally closed switch S2a, lighting the light La and closing the solenoid valve Va. This will in turn cause the fuel within the first cavity C1 to flow through the fuel flow line BC and into the carburetor allowing the piston P to move upward, and the piston base PB to again communicate with the shaft SH thereby opening the normally closed switch S2a. Therefore, the piston P will move slowly back and forth near the top of the housing H1 causing the lamp La to flash on and off. The fuel flow measuring apparatus may be manually reset by opening the first switch S1a. It should be noted, however, that if the operator does not promptly reset the fuel flow measurement apparatus as previously described the engine will nevertheless receive an adequate supply of fuel.

II. Improved Fluid Flow Measurement Apparatus

Figure 3:
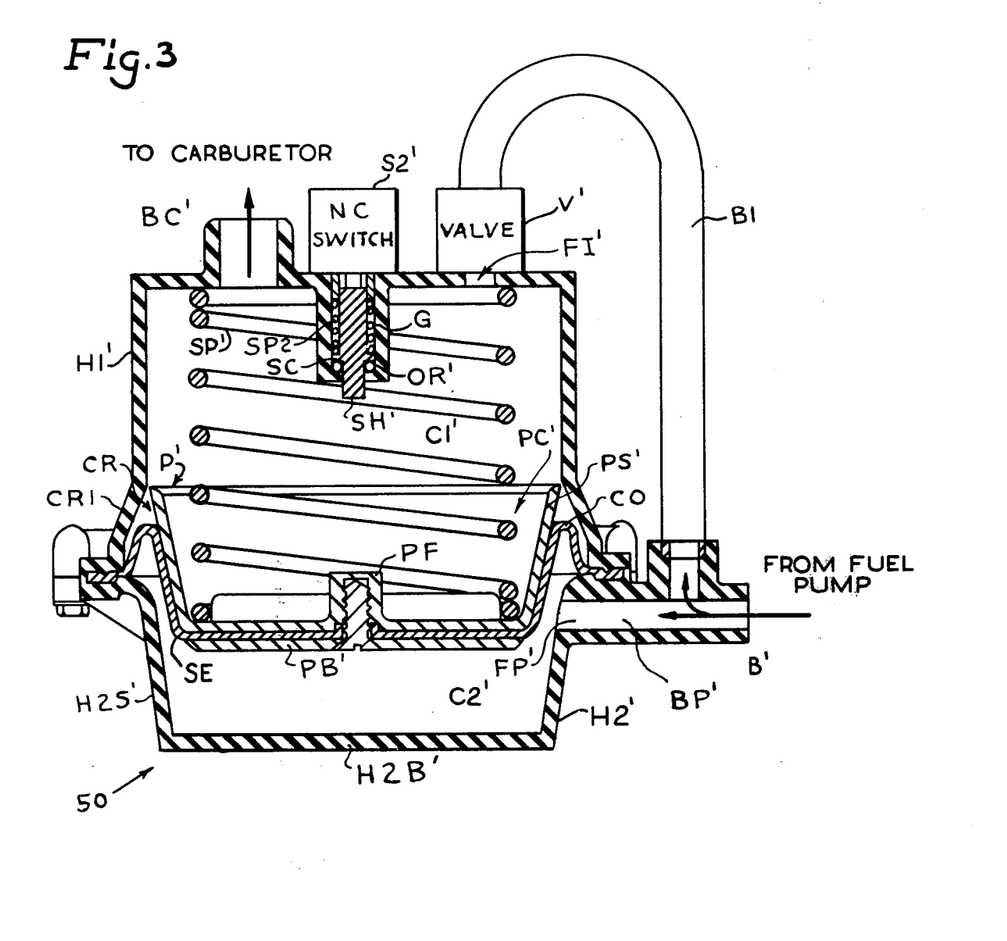
FIG. 3 shows a second preferred embodiment of the fluid flow measurement apparatus.

With specific reference to FIG. 3, an improved fluid flow measurement apparatus is shown generally as 50. The improved fluid flow measurement apparatus includes a generally cylindrical first housing H1' having at the upper end thereof a fuel flow outlet line BC' which communicates with a carburetor (not shown) of an internal combustion engine. The first housing H1' couples with a second housing H2' having a generally circular base H2B' and circumferential sides H2S' protruding upwardly therefrom. The sides H2S' taper upwardly and outwardly at an angle alpha from a perpendicular to the base H2B. The first housing H1' has a circumferential recess CR therearound adjacent to the point of attachment with the circumferential sides H2S' of the second housing H2'. This circumferential recess CR is defined by a first side CR1, an outwardly tapering generally circular surface flowing from the cylindrical portion of the first housing H1' at an angle two alpha.

A generally flexible diaphragm SE' is captured between the coupling of the first housing H1' and the second housing H2' by a plurality of fasteners FS communicating therebetween. The flexible diaphragm SE' defines a first chamber (or cavity) C1' within the first housing H1' and also defines a second cavity or chamber C2' within the second housing H2'. The flexible diaphragm SE' is attached to a circular base section PB' of a truncated conical piston P'. Tapered piston sides PS' are circumferentially attached to the piston base PB'. The piston sides PS' are tapered upwardly and outwardly from a perpendicular to the piston base PB'at an angle alpha and define therein a piston cavity PC'.

At this point it should be noted that the piston sides PS' are tapered so as to congruently couple with the tapered sides H2S' of the second housing H2'. It should also be noted that the angle alpha included between the tapered piston sides PS' and the perpendicular to the piston base PB' is approximately one-half the angle two alpha included between the first side CR1 of the circumferential recess CR and an extension circumferential surface of the housing H1'. Thus as the piston P' moves upward through the cavity C1' the radius of the convulution in the diaphragm SE' remains nearly constant as the convolution travels within the circumferential recess CR. The tapered piston sides PS' of the piston P' will be guided by the oppositely tapered sides of the circumferential recess CR of the first housing H1' as the piston P' moves longitudinally upward through the first chamber C1. This guiding function will prevent the jamming of the piston P' as it moves upward and twists or rotates within the first and second chambers C1' and C2'.

The flexible diaphragm SE' has a length sufficient to allow the base PB' of the piston P' to congruently communicate with the base H2B' of the second housing H2'. As the piston P' moves longitudinally upward from the second chamber C2' into the first chamber C1' the flexible diaphragm SE' will include a convolution or rolling section CO which will be located within the tapered sides forming the circumferential recess CR of the first housing H1'. The flexible diaphragm SE' will communicate with the tapered sides PS' of the piston P' as it moves longitudinally upward through the first chamber C1'.

The base PB' of the piston P' contains a platform PF coaxially located thereon. The platform PF is elevated for communicating with a generally cylindrical shaft SH' which communicates within a cylindrical guide G attached to the upper planar surface of the housing H1'. The shaft SH' communicates through an O-ring OR' in the guide G and is then attached to the normally closed switch S2' for the actiavation thereof. The length of the shaft SH' as it communicates with the platform PF of the piston P' is such that the normally closed switch S2' will be opened when the piston sides PS' come in close communication with the upper planar surface of the first housing H1'. Note that when the base PB' of the piston P' is in communication with the base H2B' of the second housing H2', the first chamber C1' will contain a volume equal to the predetermined volume of the fluid, or fuel, such as one-tenth of a gallon, plus the volume of the fluid contained within the piston cavity PC'.

When piston P' is in its lowermost position in housing H2' the clearance between the piston sides PS' and the side H2S' of cavity H2' is only slightly greater than the thickness of diaphragm SE'. Therefore any swelling of diaphragm SE' (as is common with flexible materials when they are exposed to gasoline) cannot cause a volume change in the area between the piston sides PS' and the side H2S' of the cavity H2'. However, the height or extension of the convolution CO and its included volume will change in some small amount. This change will not result in a metering error because when the piston P' is in the extreme up position the convolution radius is the same, as previously discussed. Therefore a similarly increased volume is induced at all piston locations by the expansion of diaphragm SE'. Thus, the sides H2S' and the diaphragm SE' are sufficiently tapered that diaphragm SE' expansion cannot mechanically jam those components as can result in a conventional straight cylindrical rolling diaphragm chamber with a narrow convolution CO radius. A wide convolution CO clearance inside a straight chamber results in greater errors in measured volume due to diaphragm expansion.

The generally cylindrical shaft SH' includes a disc shaped collar SC intermediate its ends. The diameter of the shaft collar SC is approximately equal to the inner diameter of the cavity within the guide G through which the shaft collar SC slidably moves. The O-ring OR' has an outside diameter slightly greater than the inside diameter of the cavity within the guide G, and an inside diameter slightly less than the outside diameter of the shaft SH'. With this arrangement the O-ring OR' will seal out the fuel from guide G as the shaft SH' moves therethrough. A second spring SP2 is coiled around the shaft SH' between the housing H1' and the shaft collar SC for compressing the O-ring OR' between the shaft collar SC and the end of the guide G'. This compression causes the inside diameter of the O-ring OR' to decrease and the outside diameter of the O-ring to increase, thereby improving the seal between the shaft SH' and the guide at all times except when the shaft SH' is displaced upwards.

A fuel line B' is coupled to the fuel pump (not shown) for transporting the liquid fuel or fluid through another fuel flow line B1 which communicates into the first chamber C1'. A solenoid operated valve V' regulates the flow of the fuel through fuel flow line B1 and into a first fuel inlet FI' located in the planar surface of the first housing H1' adjacent to the switch S2' and the shaft SH' attached thereto. A bypass line BP' forms a second extension of the fuel flow line B' and allows the fuel therein to flow into the second chamber C2' through a fuel port FP'. A compression spring SP' communicates between the upper planar surface of the first housing H1' and the base PB' for biasing the piston P' into close communication with the base H2B' of the second housing H2'.

The operation of the improved fluid flow measurement apparatus 50 will now be described with reference to FIG. 3, it being understood that an activation circuit comprising a momentary switch S1, an SCR and a light L, as shown in FIG. 1, is provided for the activation thereof. First, assuming that the base PB' of the piston P' is in close communication with the base H2B' of the second chamber C2', the switch S1 is momentarily activated thereby allowing the SCR to conduct a direct current which will energize the light L and close the solenoid operated valve V'. The fuel being supplied from the fuel pump through the fuel flow lines B' and BP' will then flow through the fuel port FP' and into the second chamber C2' causing the piston P' to move longitudinally upwards through the cavity C1'. The tapered sides CR1 defining the circumferential recess CR of the first housing H1' will guide the tapered sides PS' as the piston P' moves longitudinally upwards through the first cavity C1' thus expelling the predetermined volume of fuel contained therein through the fuel flow line BC' to the carburetor. As the platform PF of the piston P' communicates with the shaft SH' the normally closed switch S2' will be opened, thereby breaking the flow of the direct current through the SCR and extinguishing the light L.

The operation of the normally closed switch S2' indicates that the predetermined volume of fuel has been expelled to the carburetor through the fuel flow line BC' from the first chamber C1'. The interval required for the consumption of this predetermined volume of fuel by the engine will be indicated by the energized light L. The fuel consumption of the internal combustion engine may then be measured by multiplying the distance traveled in the period during which the light L was energized by the reciprocal of the predetermined volume of the fuel consumed by the engine during that same period.

When the flow of direct current through the light circuit L is broken by the opening of the normally closed switch S2', the solenoid operated valve V' will be simultaneously opened, thus permitting the flow of the fuel through the fuel flow line B1 and into the first chamber C1'. The pressure exerted by the compression spring SP' will cause the movement of the piston P' toward the bse H2B' of the second housing H2' thus causing the eviction of the fluid within the second cavity C2' through the fuel port FP, through the fuel flow line B1 and into the first chamber C1'. It should be noted at this point that a continuous fuel flow is provided to the carburetor both during and after the period of measurement described herein, thus preventing gaseous pockets from being introduced into the fuel flow line BC' which could cause a coughing or a sputtering of the internal combustion engine.

The switch S2' is operated by shaft SH' which is sealed into the first housing H1' by the O-ring OR'. The spring SP2 returns the shaft SH' after the activation of switch S2'. This design is particularly suitable considering the expansion inherent in O-rings exposed to gasoline, because the O-ring seals not only on the inside and outside diameters, but also on the top and the bottom due to the loading of the spring SP2.

III. Electrical Latching Circuit

An electrical latching circuit relatively impervious to noise pulses will now be described with reference to FIG. 4. This electrical circuit is a substitute for a silicon controlled rectifier (SCR) of the type described in part I of this specification, and has the advantage that careful selection of the silicon controlled rectifiers for high dv/dt capacity and bypassing for noise immunity are not required due to the unique circuit element interactions.

Figure 4:
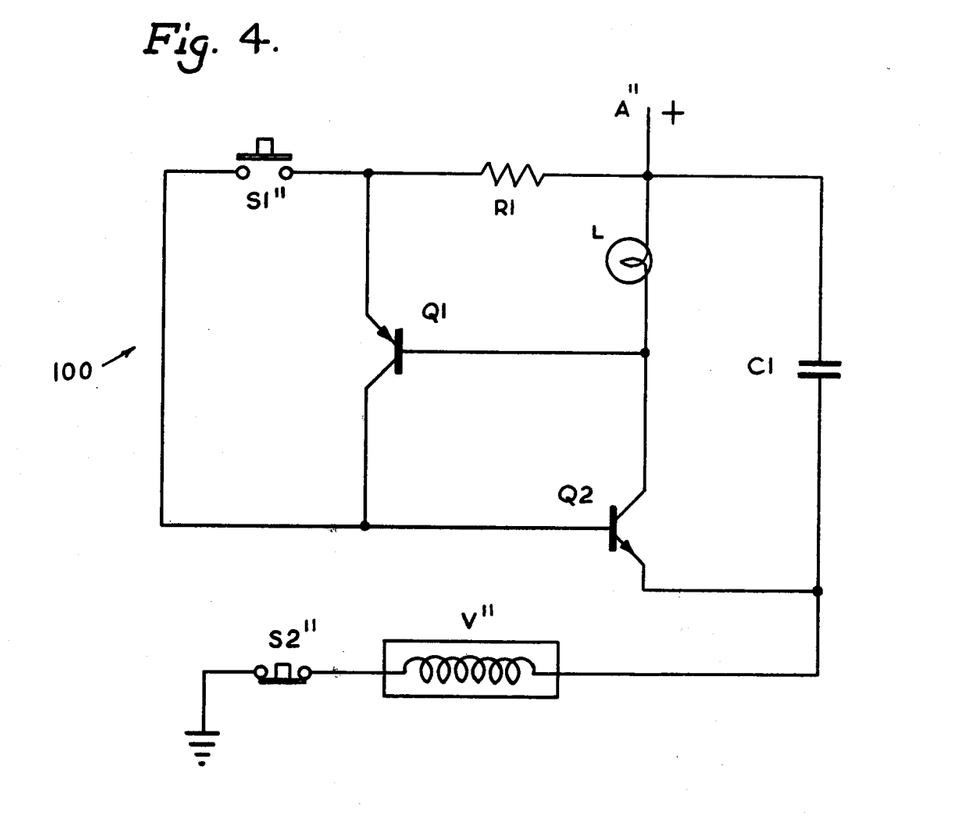
FIG. 4 shows a schemmatic diagram for an improved electrical latching circuit of the type which could be utilized in a fluid flow measurement apparatus.

The electrical direct current energy from a battery A" is controlled by the circuit, generally shown as 100 in FIG. 4, for energizing the electrical load, in this case a solenoid operated valve V''', which is connected in series with a normally closed switch S2''. The electrical latching circuit 100 comprises a variable resistance element L connected in series with the source of direct current ennergy A". This variable resistance element L has a low resistance at room temperatures, and a resistance approximately ten times the lower value of resistance when the element has been conducting a minimum current for a period of time longer than its thermal time constant T. The thermal time constant of the variable resistance element L varies in the range from 0.05 to 1.0 seconds. In the first preferred embodiment of this electrical circuit a tungsten filament lightbulb has been chosen as the variable resistance element, but other similarly reacting electrical elements may also be used. The minimum current for this tungsten filament lightbulb is approximately the current required for the filament to become incandescent.

The emitter of a first PNP driver transistor Q1 is connected to the source of direct current energy A" through an emitter resistor R1. The emitter resistor R1 is envisioned to be of a low value, approximately 100 ohms. The value of the resistor R1 is noncritical in a reasonable range centered upon the preferred value since the resistor is used only to limit the emitter to collector current of the driver transistor Q1. The base of the driver transistor Q1 is coupled to the second lead of the variable resistance element L. The collector of an NPN switching transistor Q2 is coupled to the second lead of the variable resistance element L. The base (or control element) of the switching transistor Q2 is coupled to the collector element of the first driver transistor Q1. The emitter of the switching transistor Q2 is coupled in series with the electrical load V'''. A first bypass capacitor C1 is coupled in parallel with the variable resistance element L and the switching transistor Q2. The capacitor C1 will reduce transistor dissipation and possible damage if a high frequency AC signal is induced on the associated wiring by proximity coupling to an ignition system or a radio frequency transmitter. A first switch of the normally open and momentarily closing type S1'' is coupled between the emitter and collector of the driver transistor Q1. One terminal of the second switch S2'' is coupled in series with the electrical load V''' with the opposite terminal thereof connected to the opposite pole of the source of DC electrical energy A''.

The following examples will illustrate the operation of the electrical latching circuit 100. Assume the following initial values: the resistance of the electrical load V''' is equal to 20 ohms, the resistance R1 is equal to 100 ohms, a supply voltage A'' is equal to 14 volts, a base to emitter saturation voltage of 0.7 volts for transistors Q1 and Q2, and a collector to emitter saturation voltage of 0.3 volts for Q1 and Q2. Assume further that the lamp L is a PR13 which is a commercially available tungsten filament lamp having a resistance of approximately 9 ohms when conducting 0.4 to 0.5 amps of current therethrough, and a resistance of approximately 1 ohm when not conducting and at room temperature. All of these initial values are approximately typical for silicon transistors and other elements likely to be used in this circuit.

Consider the first state in which the transistor Q2 is conducting a current which passes through the load V'''. The supply voltage of 14 volts minus the 0.3 volts of the collector to emitter saturation voltage for the transistor Q2 leaves an equivalent voltage source of 13.7 volts across the remaining elements of the circuit. These remaining elements include the lamp L and the load V'''. The resistance of these remaining elements is 20 ohms for V''' and 9 ohms for L, the total of which is 29 ohms. Utilizing Ohm's law we find that 0.47 amps will flow through the load V'''. At this current the voltage across the lamp L will be 4.25 volts (0.47 amps times 9 ohms). The voltage across the resistor R1 is therefore equal to 4.25 volts minus 0.7 volts for the base to emitter saturation voltage of the transistor Q1, the total of which is 3.55 volts. Using Ohm's law, the current through the resistor R1 is equal to 35 miliamperes. The current gain of the transistor Q1 is not critical due to the low impedance of the base driver circuit. Thereof, the minimum gain of transistor Q2 for the circuit to remain latched is derived by dividing the collector current of transistor Q2 by the base current of transistor Q2. This calculation yields 13.5 for a minimum gain of the transistor Q2 (0.47 amperes divided by 0.035 amperes). Therefore, a minimum gain specification of 20 for the transistor Q2 would be quite satisfactory.

Consider next the off or non-conducting state for the transistor Q2. Assume also that a noise pulse of sufficient amplitude to drive both transistors Q1 and Q2 into saturation has occurred, but that the duration of the noise pulse is less than T and thus is not sufficient to cause substantial heating or an increase in the resistance of lamp L. Therefore, the current through the circuit would be calculated by taking the equivalent voltage of 13.7 volts and dividing it by the equivalent resistance of 21 ohms (the 20 ohms resistance of the load V''' plus the 1 ohm resistance of the lamp L) which equals 0.65 amperes. This current causes a voltage across the lamp L to be approximately 0.65 volts which is less than the base to emitter saturation voltage of the transistor Q1.

Therefore the transistors Q1 and Q2 will remain saturated only for the duration of the noise pulse and will not thereafter be conducting. Therefore, the current through the load V" will last only for the duration of the noise pulse.

Consider next the results of changing the cold resistance of the lamp L1 from one ohm to two ohms with other values remaining the same. The current through the circuit in a period of time during which the transistors Q1 and Q2 are saturated would be calculated by taking the equivalent voltage of 13.7 volts and dividing it by the total circuit resistance of 22 ohms (the load resistance V"2 of 20 ohms plus the cold resistance of 2 ohms of the lamp L) which equals 0.62 amps. The voltage across the lamp L will then be 2 ohms times 0.62 amps or a total of 1.24 volts. The voltage across the resistance R1 will be 1.24 volts minus the emitter to base saturation voltage of 0.7 volts for a total of 0.54 volts. Therefore, the current through the resistor R1 will be 0.54 volts divided by 100 ohms, which yields a current of 5.4 miliamperes. Therefore, the required current gain of the transistor Q2 to produce an unwanted latching would be calculated by dividing the collector current of 620 miliamperes by the base current of 5.4 miliampers which yields a current gain of 115. The silicon transistors which are used for the switching transistor Q2 generally have a current gain much less than the required 115 and therefore would not latch closed even if the cold resistance of the lamp L were tiwce the nominal cold resistance of 1 ohm. Therefore, this circuit has a very broad range of operability when likely variations in element perameters are considered.

In summary, the valve V" is actuated by closing the switch S1" for a period of time greater than the thermal time constant T for the variable resistance lamp L. This will cause the transistor Q2 to be fully saturated. Therefore the voltage across the lamp L will forward bias the transistor Q1 which will in turn forward bias the transistor Q2 latching the circuit into a conductive mode. The load V" is de-energized by opening the switch S2" for a period of time greater than the thermal time constant T.

Figure 5:
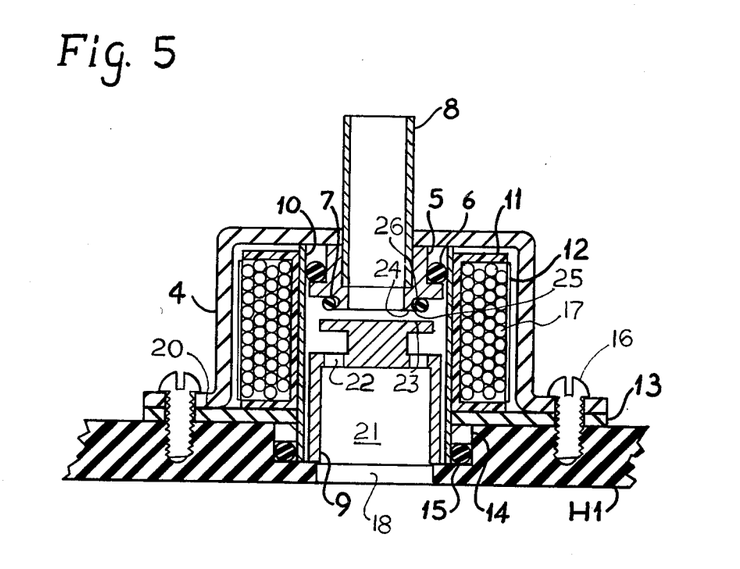
FIG. 5 is a sectional view of the solenoid valve taken on Line 5—5 of FIG. 6.
Figure 6:
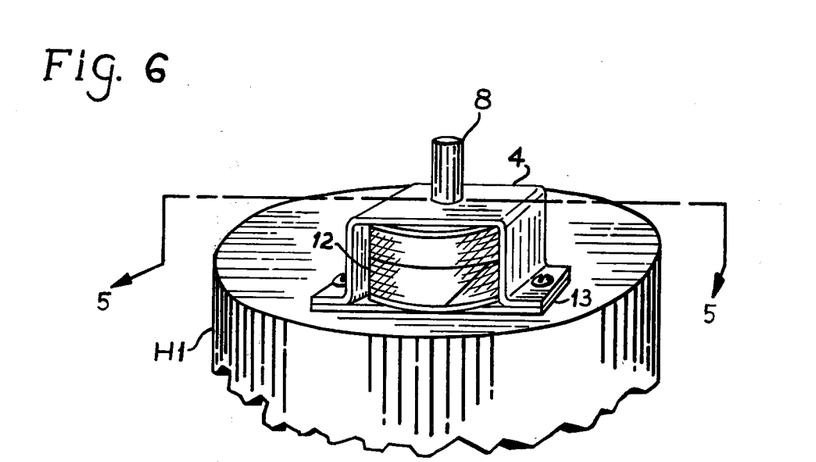
FIG. 6 is a fragmentary prospective view of the solenoid valve of the present invention.

Referring now to FIGS. 5 and 6, the solenoid valve V is more clearly illustrated attached to the housing H1 by a mounting bracket 4 by a pair of screws 16. Bracket 4 supports a central cylindrical hollow tube 10 which may be made of a non-ferrous metal such as aluminum and which has a plurality of windings 17 of a coil 12 wrapped therearound in an annular coil winding casing 11. Casing H1 has an opening 18 passing therethrough and has the central tube 10 passing into a counter sunk portion 14 and sealed with an O-ring 15. The central tube 10 also passes through a solenoid base 20 and has a slidable piston 9 mounted therein. Piston 9 has a cavity 21 and a plurality of small openings 22 leading from the cavity 21 through the piston and around a valve element 23 mounted on the piston 9. The valve element 23 is disc shaped and slides with the piston 9 against a valve seat 24 connected to an inlet pipe 8. The valve seat 24 has an annular lip 25 supporting an O-ring 26 which presses against the valve element 23 to seal between the valve element 23 and the valve seat 24 to close off the inlet pipe 8 when the piston 9 is actuated by the coil 12. Coil 12 is actuated to drive the piston 9 which may be made of a ferrous material to close the valve element 23. The valve seat 24 has a valve seat assembly 5 which includes an O-ring 6 sealing the valve seat against the central tube 10 to prevent entry of liquids into the coil assembly 12. When the current through the coil 12 is cut off, the valve element 23 in piston 9 is driven by the force of the fluid from input line 9 to an open position so that the fluid can flow through a passageway from the tube 8 around the valve element 23 in the tube 10 through the openings 22 in the piston 9 and through the cavity 21 and through the opening 18 of the casing H1. The present solenoid valve advantageously requires a very low pressure to open and close the valve in that metal to metal contact is made between the valve element 23 and the valve seat 24 thereby only compressing the O-ring 24 a sufficient distance to assure a complete seal. Thus, the power requirement is very small to energize the solenoid valve. In practice, it has been shown that less than one pound psi will seat the valve element 23 and maintain the valve closed against the fuel pump pressure applied to the liquid in input line 8.

I claim:

1. An electrical solenoid actuated fluid valve comprising in combination:
   a center tube;
   electrically actuated coil means surrounding said center tube;
   a slidable piston slidably mounted in said center tube and having a passageway therethrough and a valve element mounted thereon, said piston having first and second positions in said center tube;
   a valve seat mounted in said center tube and having an opening therethrough;
   seal means attached to said valve seat surrounding the opening therein to seal said valve element against said valve seat when said slidable piston is in said first position upon actuation of said electrically actuated coil and to open a passageway through said valve seat and through said slidable piston when said slidable piston is in said second position, whereby the valve can be opened and closed responsive to the actuation of said coil; and
   said valve seat having a seating portion and an annular flange protruding therefrom and having an O-ring attached adjacent to said flange onto said valve seat whereby said O-ring is compressed when said valve element is closed against said valve seat.

2. The apparatus in accordance with claim 4 in which said slidable piston mounted valve element is a disc shaped element fixedly attached to the top portion of said piston.

3. An electrical solenoid actuated fluid valve comprising in combination:
   a center tube;
   electrically actuated coil means surrounding said center tube;
   a slidable piston slidably mounted in said center tube and having a passageway therethrough and a valve element mounted thereon, said piston having first and second positions in said center tube;
   a valve seat mounted in said center tube having an opening therethrough;
   seal means attached to said valve seat surrounding the opening therein to seal said valve element against said valve seat when said slidable piston is in said first position upon actuation of said electrically actuated coil and to open a passageway through said valve seat and through said slidable piston when said slidable piston is in said second position, whereby the valve can be opened and closed responsive to the actuation of said coil; and said valve seat being mounted in said center tube with an O-ring seal to prevent leakage of fluid from said center tube.

4. An electrical solenoid actuated fluid valve comprising in combination:

a center tube;

electrically actuated coil means surrounding said center tube;

a slidable piston slidably mounted in said center tube and having a passageway therethrough and a valve element mounted thereon, said piston having first and second positions in said center tube;

a valve seat mounted in said center tube having an opening therethrough;

seal means attached to said valve seat surrounding the opening therein to seal said valve element against said valve seat when said slidable piston is in said first position upon actuation of said electrically actuated coil and to open a passageway through said valve seat and through said slidable piston when said slidable piston is in said second position, whereby the valve can be opened and closed responsive to the actuation of said coil;

a fluid-flow measurement device having a casing surrounding an internal cavity and having an opening therein communicating with said cavity;

a support bracket engaging said center tube in said opening in said casing; and an O-ring seal between said casing and said tube.

* * * * *